(12) United States Patent
Park et al.

(10) Patent No.: US 8,961,937 B2
(45) Date of Patent: Feb. 24, 2015

(54) METHOD FOR DETECTING AMYLOID AGGREGATES USING STYRYLPYRIDAZINE-ONE DERIVATIVES

(71) Applicant: Korea Atomic Energy Research Institute, Daejeon (KR)

(72) Inventors: Yong Dae Park, Jeollabuk-Do (KR); Jeong Hoon Park, Seoul (KR); Yong Jin Yoon, Gyeongsangnam-Do (KR); Seung Tae Yang, Jeollabuk-Do (KR); Min Goo Hur, Gyeonggi-Do (KR)

(73) Assignee: Korea Atomic Energy Research Institute, Daejeon (KR)

( * ) Notice: Subject to any disclaimer, the term of this patent is extended or adjusted under 35 U.S.C. 154(b) by 0 days.

(21) Appl. No.: 13/802,322

(22) Filed: Mar. 13, 2013

(65) Prior Publication Data

US 2014/0134109 A1    May 15, 2014

(30) Foreign Application Priority Data

Nov. 14, 2012    (KR) ........................ 10-2012-0129067

(51) Int. Cl.
| | | |
|---|---|---|
| *A61B 5/00* | (2006.01) | |
| *A61B 8/00* | (2006.01) | |
| *A61B 10/00* | (2006.01) | |
| *A61K 49/00* | (2006.01) | |
| *C07D 237/14* | (2006.01) | |

(52) U.S. Cl.
CPC ............ *A61K 49/006* (2013.01); *C07D 237/14* (2013.01)
USPC .............................. 424/9.6; 544/241; 436/86

(58) Field of Classification Search
CPC combination set(s) only.
See application file for complete search history.

(56) References Cited

PUBLICATIONS

Kim et al. J. Heterocyclic Chem. 46, 691 (2009) 691-701.*
Kung et al. JACS 2001, 123, 12740-12741.*
Park et al. (2012) "Fluorescent 2-Styrylpyridazin-3(2H)-One Derivatives as Probes Targeting Amyloid-Beta Plaques in Alzheimer's Disease," Bioorganic & Medicinal Chemistry Letters 22:4106-4110.

* cited by examiner

*Primary Examiner* — Michael G Hartley
*Assistant Examiner* — Sean R Donohue
(74) *Attorney, Agent, or Firm* — Morrison & Foerster LLP (57) ABSTRACT

The present invention relates to a composition for detecting beta amyloid aggregates and a composition for diagnosing beta amyloid aggregation disease, comprising a 2-styrilpyridizine-3(2H)-one derivative or its pharmaceutically acceptable salt, to a diagnostic kit for diagnosing beta amyloid aggregation disease comprising said composition and to a method for detecting beta amyloid aggregates using said compositions to provide information for beta amyloid aggregation disease diagnosis.

7 Claims, 3 Drawing Sheets

METHOD FOR DETECTING AMYLOID AGGREGATES USING STYRYLPYRIDAZINE-ONE DERIVATIVES

CROSS-REFERENCE TO RELATED APPLICATION

This application claims the benefit of priority to Korean Patent Application No. 10-2012-0129067, filed on Nov. 14, 2012, the content of which is incorporated by reference herein in its entirety.

BACKGROUND OF THE INVENTION

1. Field of the Invention

The present invention relates to a composition for detecting beta amyloid aggregates and a composition for diagnosing beta amyloid aggregation disease, comprising 2-styrilpyridizine-3(2H)-one derivatives or its pharmaceutically acceptable salt, and a fluorescence reagent for detecting beta amyloid aggregates comprising the composition for detecting beta amyloid aggregates, and a diagnostic kit for diagnosing beta amyloid aggregation disease comprising the composition for diagnosing beta amyloid aggregation disease.

Also, the present invention relates to a method for detecting beta amyloid aggregates, comprising using 2-styrilpyridizine-3(2H)-one derivatives or its pharmaceutically acceptable salt to provide information for beta amyloid aggregation disease diagnosis.

2. Background of the Invention

Data of the Ministry of Health and Society show that the number of dementia patients was nearly 280,000 in 1998, and raised to 400,000 in 2002, domestically. According to Alzheimer's disease association data in the United States, four million people suffer from Alzheimer and it is estimated that the number may reach fourteen million people in 2050. It is estimated that twenty-two million people will be troubled with Alzheimer worldwide in 2005.

The main reason for the sharp increase in the number of dementia patients throughout the world is aging in society. As an average life is increased, aging population has been increased to naturally increase the number of dementia patients. Korea, which has achieved the rapid economic growth, is quickly transforming into an aging society, and thus, an attack rate of senile dementia, stroke, Parkinson's disease represented by Alzheimer's disease is on the rise. Improved data of the United Nations Food and Agriculture Organization (FAO) estimate that a population growth of an age group older than 60 is global trends, and even in Asia, senior citizens over sixty is anticipated to be jumped from 8% of the general population in 2000 to 25% as of 2050. The graying and the attack rate of dementia are very closely related. In Korea, 15% of aging population by age 75 to 79 suffers from dementia, and 39% of aging population over age 80 is dementia patents. Also, a dementia prevalence rate of women is higher than men, but the precise cause is unknown and the medical world in many countries has sought to find the cause competitively.

Alzheimer's disease is a progressive neurodegenerative disease featuring a reduction in cognitive ability, irreversible memory loss, a loss of sense of direction, and language capabilities impairment as nerve cells of the brain are reduced Alzheimer's patients have a plurality of senile plaques comprised of numerous neurofibrillary tangles (NFT) formed by beta amyloid (Aβ) peptide, and hyperphophorylated-tau protein fiber in the brain (Ginsberg, S. D., et al., "Molecular Pathology of Alzheimer's Disease and Related Disorders," in Cerebral Cortex: Neurodegenerative and Age-related Changes in Structure and Function of Cerebral Cortex, Kluwer Academic/Plenum, NY (1999), pp. 603-654; Vogelsberg-Ragaglia, V., et al., "Cell Biology of Tau and Cytoskeletal Pathology in Alzheimer's Disease," Alzheimer's Disease, Lippincot, Williams & Wilkins, Philadelphia, Pa. (1999), pp. 359-372). Whether beta amyloid is a direct cause or a result of a cause of Alzheimer's disease is still uncertain, but so far, aggregates based on accumulation of beta amyloid has been the most typical syndrome or hallmark of Alzheimer's disease. Thus, ADNI (Alzheimer's Disease Neuroimaging Initiative) organized by NIA (National Institute of Aging) in the US in 2004 labeled beta amyloid aggregates as the most powerful biomarker of Alzheimer's disease, and thus, quantizing accumulation of aggregates of beta amyloid by using a noninvasive biomolecular image may make breakthrough in an early eiagnosis and treatment of Alzheimer's disease, and the process of Alzheimer's disease may be suppressed by injecting drug suppressing formation of beta amyloid aggregates and tangles.

Compounds having fluorescence that may be easily bound to beta amyloid aggregates to readily indicate the presence have been actively researched in order to diagnose diseases that may be diagnosed by quantitatively detecting beta amyloid aggregates including Alzheimer's disease. A typical one of such compounds is congo red (CR), and Alzheimer's disease may be definitely diagnosed by conducting a postmortem and staining the brain with congo red. However, this method cannot be used for a living person. The reason is because congo red is strongly water-soluble, which is, thus, cannot pass through brain blood barrier (BBB), so, although it is injected to a living person, it cannot enter the brain. Thus, a marker that may be bound to beta amyloid aggregates and tangles and able to pass through BBB may be injected into a human body and a distribution thereof in the brain may be imaged to thereby diagnose a disease pathologically featuring accumulation of beta amyloid aggregates such as Alzheimer's disease, or the like, Besides congo red, one of the first developed compounds is derivatives of Chrysamine-G, but it is also too low a level to pass through the BBB, making it impossible to be used in actuality. (Klunk W E, Debnath M L, Pettegrew J W. Development of small molecule probes for the beta amyloid protein of Alzheimer's disease. Neurobiol Aging 1994; 15:691-8. Klunk W E, Debnath M L, Pettegrew J W. Chrysamine-G binding to Alzheimer and control brain: Autopsy study of a new amyloid probe. Neurobiol Aging 1995; 16:541-8.)

Afterwards, as 6-dialkylamino-2-naphthylethylidene (FDDNP) derivatives and thioflavin-T (ThT)-based derivatives were developed, research was activated. (Agdeppa E D, Kepe V, Liu J, Flores-Tones S, Satyamurthy N, Petric A, Cole G M, Small G W, Huang S C, Barrio J R. Binding properties of radiofluorinated 6-dialkylamino-2-naphthylethylidene derivatives as positron emission tomography imaging probes for β-amyloid plaques in Alzheimer's disease. J Neuroscience 2001; 21:1-5. Mathis C A, Bacskai B J, Kajdasz S T, MlLellan M E, Frosch M P, Hyman B T, Holt D P, Wang Y, Huang G-F, Debnath M L, Klunk W E. A lipophilic thioflavin-T derivative for positron emission tomography (PET) imaging of amyloid in brain. Bioorg Med Chem Lett 2002; 12:295-298.)

Also, various benzothiazole derivatives and stilbene derivatives were filed for patent as radioactive isotope labeled compounds that may be able to image beta amyloid. (US Patent Pub. No. 2002/0133019 A1, W. E. Klunk, C. A. Mathis Jr, Thioflavin derivatives for use in antemortem diagnosis of Alzheimer's disease and vivo imaging and prevention of amyloid deposition; US Patent Pub. No. 2003/0149250 A1, H. F. Kung, M-P. Kung, Z-P. Zhuang, Stilbene derivatives and their use for binding and imaging amyloid plaques).

However, the currently developed beta amyloid detecting fluorescence legand has a complicate preparation process, a large molecular mass, and does not show a great change in fluorescence properties when it is bound with beta amyloid aggregates. Also, it is bound also with phosphorylated tau protein fiber, rather than selectively only with beta amyloid, so it does not have high detection selectivity. Also, the beta amyloid detecting fluorescence legand has a low uptake rate in an animal testing, and it is not easy to remove legand from the brain, having a difficulty in using it in actuality.

Due to the problems of the conventional beta amyloid detecting legands, demand for the development of a specific reagent in terms of diagnosis reagent for staining beta amyloid aggregates that may be able to overcome the problems has continued.

RELATED ART DOCUMENT

US Patent Laid Open Publication No. US 20080038195 A1
Japanese Patent Laid Open Publication No. JP 2004506723 A
Japanese Patent Laid Open Publication No. JP 2009511583 A

SUMMARY OF THE INVENTION

Therefore, an aspect of the detailed description is to provide a composition for detecting beta amyloid aggregates, comprising 2-styrilpyridizine-3(2H)-one derivatives or its pharmaceutically acceptable salt, a composition for diagnosing beta amyloid aggregation disease, comprising 2-styrilpyridizine-3(2H)-one derivatives or its pharmaceutically acceptable salt, and to provide a fluorescence reagent for detecting beta amyloid aggregates and a diagnostic kit for diagnosing beta amyloid aggregation disease, each comprising the foregoing composition.

Another aspect of the detailed description is to provide a method for detecting beta amyloid aggregates, comprising using 2-styrilpyridizine-3(2H)-one derivatives or its pharmaceutically acceptable salt to provide information for beta amyloid aggregation disease diagnosis.

To achieve these and other advantages and in accordance with the purpose of this specification, as embodied and broadly described herein, in an aspect, there is provided a composition for detecting beta amyloid aggregates, comprising 2-styrilpyridizine-3(2H)-one derivatives represented by Chemical Formula (1) shown below or its pharmaceutically acceptable salt.

Chemical formula (I)

Wherein, R is independently selected from the group consisting of hydrogen, halogen, cyano, substituted or unsubstituted carbonyl, nitro, substituted or unsubstituted $C_1$-$C_{10}$ alkyl, substituted or unsbustituted phenyl, substituted or unsubstituted $C_1$-$C_{10}$ alkenyl, substituted or unsubstituted amino, and substituted or unsubstituted $C_1$-$C_{10}$ alkoxy, and n is an integer of 1 to 3.

In another aspect, there is provided a composition for diagnosing beta amyloid aggregates aggregation disease, comprising 2-styrilpyridizine-3(2H)-one derivatives represented by Chemical formula (1) or its pharmaceutically acceptable salt.

Description of Chemical formula (1) is the same as that described above, so a repeated description thereof will be omitted.

In another aspect, there is provided a method for detecting beta amyloid aggregates, comprising using 2-styrilpyridizine-3(2H)-one derivatives represented by Chemical formula (1) or its pharmaceutically acceptable salt to provide information for beta amyloid aggregation disease diagnosis.

Description of Chemical formula (1) is the same as that described above, so a repeated description thereof will be omitted.

In another aspect, there is provided a fluorescence reagent for detecting beta amyloid aggregates, comprising the composition for detecting beta amyloid aggregates.

In another aspect, there is provided a diagnostic kit for diagnosing beta amyloid aggregation disease, comprising the composition for detecting beta amyloid aggregates.

The present invention will be described in detail.

An embodiment of the present invention includes a composition for detecting beta amyloid aggregates, comprising 2-styrilpyridizine-3(2H)-one derivatives represented by Chemical formula (1) below or its pharmaceutically acceptable salt.

Chemical formula (1)

Wherein, R is independently selected from the group consisting of hydrogen, halogen, cyano, substituted or unsubstituted carbonyl, nitro, substituted or unsubstituted $C_1$-$C_{10}$ alkyl, substituted or unsbustituted phenyl, substituted or unsubstituted $C_1$-$C_{10}$ alkenyl, substituted or unsubstituted amino, and substituted or unsubstituted $C_1$-$C_{10}$ alkoxy, and n is an integer of 1 to 3.

Another embodiment of the present invention includes a composition for diagnosing beta amyloid aggregation disease, comprising 2-styrilpyridizine-3(2H)-one derivatives represented by Chemical formula (1) or its pharmaceutically acceptable salt.

Chemical formula (I)

Wherein, R is independently selected from the group consisting of hydrogen, halogen, cyano, substituted or unsubstituted carbonyl, nitro, substituted or unsubstituted $C_1$-$C_{10}$ alkyl, substituted or unsbustituted phenyl, substituted or unsubstituted $C_1$-$C_{10}$ alkenyl, substituted or unsubstituted amino, and substituted or unsubstituted $C_1$-$C_{10}$ alkoxy, and n is an integer of 1 to 3.

Preferably, in Chemical formula (1), R may be independently selected from the group consisting of hydrogen, halogen, cyano, $C_1$-$C_3$ alkoxy carbonyl, nitro, $C_1$-$C_3$ alkyl, phenyl, phenylvinyl, $C_1$-$C_3$ dialkyl amino, amino, and $C_1$-$C_3$ alkoxy.

Preferably, in Chemical formula (1), R may be selected from the group consisting of hydrogen, halogen, cyano, methoxy, carbonyl, nitro, methyl, phenyl, phenylvinyl, dimethyl amino, amino, and methoxy.

More preferably, the 2-styrilpyridizine-3(2H)-one derivatives may be (E)-4,5-dichloro-2-(4-(dimethylamino)styril) pyridizine-3(2H)-one.

Detection of the beta amyloid aggregates is made by "binding" between effective components such as styrilpyridizine-3(2H)-one derivatives, and the like, and amyloid aggregates, and "binding" refers to a chemical interaction. Thus, examples of binding may include covalent bond, ionic bond, hydrophilic-hydrophilic interaction, hydrophobic-hydrophobic interaction, and complex compound bond.

"Pharmaceutically acceptable salt" used in the present invention refers to carboxylic acid salt or acid addition salt of the 2-styrilpyridizine-3(2H)-one derivatives of the present invention which is in contact with a tissue of a subject and appropriately used, does not have an inappropriate toxicity, stimulation, an allege reaction, or the like, and is effective for the intended purpose with reasonable beneficial expenses/risk ratio within a sound determination range, and its zwitter ion if possible. The term 'salt' refers to relatively non-toxic inorganic and organic acid addition salt of a compound. Also, salt includes salt derived from aliphatic mono and dicarboxylic acid, e.g., acetic acid, phenyl-substituted alkanoic acid, hydroxy alkanoic acid, and alkandic acid, and non-toxic organic acid such as aromatic acid, and aliphatic acid, and aromatic sulfonic acid. These salts may be prepared while a compound is finally isolated or purified in situ. A free base form of the purified compound is separately reacted with an appropriate organic acid or inorganic acid and the thusly formed salt is isolated to be prepared. A typical addition salt includes hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthalate, mesilate, glucoheptonate, lactiobionate, and laurylsulfonate salt, propionate, pivalate, cyclamate, isethionate, and the like. These may include cation using alkali and alkaline earth metal, e.g., sodium, lithium, potassium, calcium, magnesium, and the like, as a substrate, non-toxic ammonium including ammonium, tetramethylammonium, tetraethylammonium, methylamine, dimethylamine, trimethylamine, triethylamine, ethylamine, and the like, which, however, is not limited thereto, quaternary ammonium, and amine cation.

The term "amyloid aggregates" used in the present invention refers to a aggregation state in which various insoluble fibrous proteins are deposited in tissues of a patient. Amyloid aggregates include aggregates formed as amyloid protein aggregates and/or an amyloid deposit formed by additional combination of amyloid protein.

The composition may be oral-administered or parenteral-administered in actual clinical trials, and may be used in the form of general pharmaceutical preparations.

Namely, the composition according to the present invention may be administered in various forms such as an oral or parenteral form in actual clinical trials, and when the composition is medicated, it may be prepared by using a diluents or excipient such as a filler, a bulking agent, a binder, a wetting agent, a disintegrant, a surfactant, or the like. A solid preparation for oral administration may include a tablet, a pellet, powders, granules, capsules, and the like, and such solid preparation may be prepared by mixing at least one or more excipients, e.g., starch, calcium carbonate, sucrose, lactose, gelatin, and the like, in the compound. Also, besides the simple excipients, lubricants such as magnesium state talk may also be used.

Liquid medication for oral administration corresponds to a suspension, a liquid for internal use, an emulsion, syrup, or the like. Besides water, a liquid paraffin, frequently used simple diluent, various excipients, e.g., a wetting agent, a sweeting agent, a flavoring agent, a preserved agent, or the like, may be included. Medication for parenteral administration may include a sterilized aqueous solution, non-aqueous solvent, a suspension, an emulsion, alyophilized preparation, and a suppository. As the non-aqueous solvent and the suspension, propylene glycol, polyethylene glycol, vegetable oil such as olive oil, injectable ester such as ethyl oleate, or the like, may be used. As a mechanism of suppository, witepsol, macrogol, tween 61, cocoa butter, laurinum, glycerol gelatine, and the like, may be used. Also, calcium or vitamin D3 may be added in order to prevent a beta amyloid aggregation disease represented by Alzheimer's disease or promote efficiency as a medicine.

In order to prevent a beta amyloid aggregation disease represented by Alzheimer's disease or treat it, the composition according to the present invention may be used alone or may be used together with methods using an operation, a radiation therapy, a hormone therapy, a chemical therapy, and a biological reaction regulator.

In the present invention, the beta amylid aggregation disease generally refers to a disease featuring aggregation of beta amyloid as pathological characteristics. In order to detect beta amyloid aggregates, the present invention may provide a composition comprising 2-styrilpyridizine-3(2H)-one derivatives represented by Chemical Formula (1) shown above, which is specifically bound to the aggregates or its pharmaceutically acceptable salt, and also provide a composition comprising 2-styrilpyridizine-3(2H)-one derivatives or its pharmaceutically acceptable salt, capable of diagnosing a beta amyloid aggregation disease through specific binding with beta amyloid aggregates.

The beta amyloid aggregation disease may be selected from the group consisting of dementia, Alzheimer's disease, Down's syndrome, amyloid angiopathy, cerebral amyloid angiopathy, generalized amyloidosis, Dutch type amyloidosis, inclusion-body myositis, Mediterranean fever, Muckle-Wells syndrome, idiopathic myeloma, amyloid polyneuropathy, amyloid cardiomyopathy, generalized senile amyloidosis, amyloidosis hereditary cerebral hemorrphage, Down's syndrome, scrapie, Creutzfeldt-Jakob disease, kuru disease, Gerstmann Straussler Scheinker syndrome, medullary carcinoma, muscular atrophy disease, and langerhans islets II-type diabetes mellitus.

In case in which the beta amyloid aggregation disease is Alzheimer's disease, a diagnosis composition is required to have a sufficient lipotropy so as to be diffused to cell membrane in order to pass through the brain blood bather (BBB). Also, an ideal Alzheimer's disease may be quickly ingested in the brain of a normal person and discharged to outside of the consumer without a short time without being involved in any metabolism.

In another embodiment of the present invention, in order to provide information for beta amyloid aggregation diagnosis, another embodiment of the present invention includes a method for detecting beta amyloid aggregates, comprising 2-styrilpyridizine-3(2H)-one derivatives represented by Chemical Formula (1) shown below or its pharmaceutically acceptable salt.

Chemical formula (I)

Chemical formula (I)

Wherein, R is independently selected from the group consisting of hydrogen, halogen, cyano, substituted or unsubstituted carbonyl, nitro, substituted or unsubstituted $C_1$-$C_{10}$ alkyl, substituted or unsbustituted phenyl, substituted or unsubstituted $C_1$-$C_{10}$ alkenyl, substituted or unsubstituted amino, and substituted or unsubstituted $C_1$-$C_{10}$ alkoxy, and n is an integer of 1 to 3.

Preferably, in Chemical formula (1), R may be independently selected from the group consisting of hydrogen, halogen, cyano, $C_1$-$C_3$ alkoxy carbonyl, nitro, $C_1$-$C_3$ alkyl, phenyl, phenylvinyl, $C_1$-$C_3$ dialkyl amino, amino, and $C_1$-$C_3$ alkoxy.

Preferably, in Chemical formula (1), R may be selected from the group consisting of hydrogen, halogen, cyano, methoxy, carbonyl, nitro, methyl, phenyl, phenylvinyl, dimethyl amino, amino, and methoxy.

More preferably, the 2-styrilpyridizine-3(2H)-one derivatives may be (E)-4,5-dichloro-2-(4-(dimethylamino)styril) pyridizine-3(2H)-one.

In order to prevent a beta amyloid aggregation disease represented by Alzheimer's disease or treat it, the composition according to the present invention may be used alone or may be used together with methods using an operation, a radiation therapy, a hormone therapy, a chemical therapy, and a biological reaction regulator.

In the present invention, the beta amylid aggregation disease generally refers to a disease featuring aggregation of beta amyloid as pathological characteristics. By providing the composition comprising 2-styrilpyridizine-3(2H)-one derivatives represented by Chemical Formula (1) shown above, which is specifically bound to the aggregates or its pharmaceutically acceptable salt in order to detect beta amyloid aggregates, the present invention may provide a method for detecting beta amyloid aggregates for providing information for diagnosing beta amyloid aggregates by using it.

The beta amyloid aggregation disease may be selected from the group consisting of dementia, Alzheimer's disease, Down's syndrome, amyloid angiopathy, cerebral amyloid angiopathy, generalized amyloidosis, Dutch type amyloidosis, inclusion-body myositis, Mediterranean fever, Muckle-Wells syndrome, idiopathic myeloma, amyloid polyneuropathy, amyloid cardiomyopathy, generalized senile amyloidosis, amyloidosis hereditary cerebral hemorrhage, Down's syndrome, scrapie, Creutzfeldt-Jakob disease, kuru disease, Gerstmann Straussler Scheinker syndrome, medullary carcinoma, muscular atrophy disease, and langerhans islets II-type diabetes mellitus.

The method for detecting beta amyloid aggregates may comprise: introducing a detectable amount of a composition comprising 2-styrilpyridizine-3(2H)-one derivatives or its pharmaceutically acceptable salt to a cell or a subject; permitting a period of time for the 2-styrilpyridizine-3(2H)-one derivatives or its pharmaceutically acceptable salt to be bound with beta amyloid aggregates to form a fluorescence marker; and detecting the fluorescence marker.

The detecting of the fluorescence marker may be performed by using a single photon emission computed tomography (SPECT) as a nuclear medical analysis method or a positron emission tomography (PET), and in particular, by imaging it in real time by using the PET.

In the imaging, in a first step, a detectable amount of the composition comprising 2-styrilpyridizine-3(2H)-one derivatives or its pharmaceutically acceptable salt is introduced to tissues or a patient. The compound is typically part of a pharmaceutical composition, and may be administered to tissues or a subject according to a method known to a person skilled in the art.

Administration of the composition to a patient may be performed by systematic or topical administration path. For example, the composition may be administered through oral, rectal, parenteral (intravenous, intramuscular, subcutaneous), intracisternal, vaginal, intraperitoneal, intravescial, topical (powder, ointment, or dripping) or bucal, or intranasal spray. The composition may be administered to a subject such that it may move through a body. Alternatively, the composition may be administered to an interested particular organ or tissues. For example, it may be preferable to determine a position of amyloid aggregates within a brain and quantize the same. One of the most necessary characteristics in in vivo imaging of a brain is capability of an effective component to pass through brain blood barrier (BBB) without being damaged after bolus intravenous injection of the effective component.

In the method for detecting beta amyloid aggregates, a detectable amount of the composition comprising 2-styrilpyridizine-3(2H)-one derivatives or its pharmaceutically acceptable salt is introduced into the subject, and after a sufficient period of time for the compound to be bound with the amyloid aggregates has passed, a fluorescence marker may be detected in a noninvasive manner from the subject. Alternatively, a tissue sample is separated from the subject, and the composition is introduced into the tissue sample. After a sufficient period of time for the 2-styrilpyridizine-3 (2H)-one derivatives, or the like, of the composition to be bound with the amyloid aggregates has passed, a fluorescence marker may be detected.

The term of "tissue" refers to part of a body of the subject. The tissue may include, for example, brain, heart, liver, blood vessel, and artery. The detectable amount is an amount of the composition required for detecting through the selected detecting method. The amount of the composition introduced into the patient for detection may be easily determined by a person skilled in the art. For example, the composition may be administered into the subject by increasing an amount thereof until when an effective component of the composition is detected according to a selected detection method.

The term "subject" refers to a human or other animals. A person skilled in the art is accustomed to determining a sufficient period of time for the 2-styrilpyridizine-3(2H)-one derivatives, or the like, to be bound with the amyloid aggregates. A required period of time may be easily determined by introducing a detectable amount of the composition to the subject, and subsequently detecting a marker at various points in time after the administration.

Another embodiment of the present invention includes a fluorescence reagent for detecting beta amyloid aggregates, comprising a composition for detecting the beta amyloid aggregates.

Another embodiment of the present invention includes a beta amyloid aggregation disease diagnostic kit comprising a composition for diagnosing the beta amyloid aggregates.

In the present invention, a ligand specifically bound with fibrous Aβ aggregates is developed and results in detecting the aggregates and diagnosing beta amyloid aggregation disease.

The composition comprising 2-styrilpyridizine-3(2H)-one derivatives, or the like, may be used as an in vivo diagnostic tool and as a probe for visualizing progressive deposition of Aβ in research of AD amyloid formation of a survival patient.

Currently, amyloid is detected through a histological analysis of biopsy or autopsy. However, autopsy is disadvantageous in that it can be used only for paragnosis, or the like. Thus, the present invention is excellent in that it provides a simple non-invasive method for detecting amyloid aggregates from a patient and quantizing the same, which is urgently requested currently.

Imaging Aβ aggregates from the brain has some potential advantages. Imaging technique can improve a diagnosing method by checking a latent patient who has an excessive amount of Aβ aggregates in the brain so has a high possibility of an attack of Alzheimer's disease. Also, the technique may be useful to monitor the progress of Alzheimer's disease. When an anti-beta amyloid medication treatment is available, imaging of the Aβ aggregates of the brain may provide an important means for monitoring a treatment.

The reason why it is difficult to directly image amyloid aggregates within a living body is because aggregates have the same physical properties, e.g., density and moisture content, as those of normal tissues in many aspect. For this reason, attempts for imaging amyloid aggregates by using MRI and CAT resulted in disappointment and efforts for labeling amyloid aggregates with antibody, serum amyloid P protein or other probe molecules provided some selectivity with respect to peripheral portions of tissues, but provide poor images with respect to the inside of tissues.

A latent legand for detecting Aβ aggregates of brain of a living subject should traverse undamaged BBB. Thus, brain introduction may be made only by using a legand having relatively small molecular size and high lipophilicity, and 2-styrilpyridizine-3(2H)-one derivative according to the present invention is a compound satisfying such requirements, which, thus, may provide a huge breakthrough for diagnosing beta amyloid aggregates.

An existing beta amyloid aggregates detection fluorescence legands are prepared by a complicated preparation processes and have molecular weight of 600 Da or more, but 2-styrilpyridizine-3(2H)-one derivatives, or the like, of the present invention is prepared by a simple preparation process and has an appropriate molecular weight of about 300 Da, satisfying the foregoing conditions.

Also, the existing fluorescence legand does not show a great change in fluorescence properties after being bound with aggregates, but the 2-styrilpyridizine-3(2H)-one derivatives, or the like, shows fluorescence intensity of 40 times or more and a great change in fluorescent properties after being bound with beta amyloid aggregates. The compound detecting beta amyloid aggregates with the high level of sensitivity as described above and the detecting method and the diagnosing method using the compound are first proposed in the present invention.

As a result, in comparison to existing radio isotope label dementia diagnosis compounds, the 2-styrilpyridizine-3(2H)-one derivatives, or the like, according to the present invention have advantages in that they have a small molecular weight without assuming charges, have a high uptake rate in animal experiment, are easily removed from the brain, and are selectively bound with amyloid.

Thus, by using the excellent binding properties of the 2-styrilpyridizine-3(2H)-one derivatives, or the like, with beta amyloid aggregates, a diagnostic kit and imaging product for measuring beta amyloid aggregates can be made, and in addition, a detecting product for searching a material for suppressing formation of beta amyloid aggregates (medicine for dementia) may also be made. In addition, the composition comprising the 2-styrilpyridizine-3(2H)-one derivatives or its pharmaceutically acceptable salt for detecting beta amyloid aggregates or diagnosing beta amyloid aggregation disease, and the method for detecting beta amyloid aggregates for diagnosing beta amyloid aggregation disease are expected to become an original technology of the development of radiopharmaceuticals of styrylpyridazine-one.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from the detailed description.

BRIEF DESCRIPTION OF THE DRAWINGS

The accompanying drawings, which are included to provide a further understanding of the invention and are incorporated in and constitute a part of this specification, illustrate exemplary embodiments and together with the description serve to explain the principles of the invention. In the drawings.

(F) Microscope fluorescence image of SHSY5Y cell extract (culture with Aβ42+ staining with thio-flavine T)

DETAILED DESCRIPTION OF THE INVENTION

Hereinafter, embodiments of the present invention will now be described in detail with reference to the accompanying drawings. The invention may, however, be embodied in many different forms and should not be construed as being limited to the embodiments set forth herein.

1. Preparation of 1.2-styrylpyridazine-3(2H)-one Derivative (1) Synthesis of 4,5-dichloro-2-chloromethylpyridazine-3(2H)-one 4,5-dichloripyridazine-3(2H)-one (60 g, 364 mmol) and distilled water 350 mL) were stirred at room temperature for 10 minutes. A formaldehyde solution (36%, 70 mL) were added and refluxed for 1.5 hours. The resulting material was cooled down to 5-10° C., and the produced precipitate was filtered, washed with cold water (0-5° C., 200 mL), and dried in the air to obtain N-hydroxymethyl-4,5-dichloropyridazine-3(2H)-one. A methylene chloride solution (50 mL) of thionyl chloride (357 mmol) and dimethyl formamide (360 mmol) was slowly added to a mixture of the N-hydroxymethyl-4,5-dichloropyridazine-3(2H)-one and methylene chloride (550 mL) and methylene chloride (550 mL) at room temperature for 30 minutes with stirring. The mixture was stirred at room temperature for 2 hours. After the mixture was cooled down to 0° C., water (200 mL) was slowly added. The solution was neutralized to pH 6.7-7.4 by using NaHCO$_3$ saturated solution. An organic layer was separated and dried on anhydrous magnesium sulfate. The organic solution was evaporated to concentrated under reduced pressure. The residue was washed with n-hexane (100 mL) to obtain 4,5-dichloro-2-chloromethylpyridazine)-3(2H)-one (71.2 g, 92%). White crystal (diethyl ether/n-hexane=1:5, v/v). mp 69-70° C. TLC (CH$_2$Cl$_2$) Rf=0.65. IR (KBr) 3046, 2984, 1670, 1292, 1122, 964 cm$^{-1}$; 1H NMR (CDCl$_3$): δ 5.83 (s, 2H), 7.88 ppm (s, 1H); $^{13}$C NMR (CDCl$_3$) δ 58.40, 134.87, 137.23, 137.34, 155.58 ppm. Elemental analysis calcd. for C$_5$H$_3$Cl$_3$N$_2$O: C, 28.13; H, 1.42; N, 13.12. Found: C, 28.10; H, 1.41; N, 13.09.

(2) Method of synthesizing trans-4,5-dichloro-2-styrylpyridazine-3(2H)-one 4,5-dichloro-2-chloromethylpyridazine-3(2H)-one (3 g, 14.055 mmol), potassium iodide (2.45 g, 14.76 mmol), and acetonitril (50 mL) were refluxed for 10 hours. The resulting material was cooled down to 30-40° C., and triphenylphosphine (4.07 g, 15.51 mmol) was added to the reaction solution. Thereafter, the mixture was refluxed for 6 hours, cooled at room temperature, filtered by using Celite 545, and washed with methylene chloride (50 mL). An organic layer was concentrated under reduced pressure. Dichloromethane (100 mL was added, and the solution was stirred for 20 minutes. The solution was filtered and concentrated under reduced pressure. The solution was cooled down to room temperature, obtained precipitate was filtered, washed with an excessive amount of diethyl ether, and dried to obtain pale yellow crystal product. The product was used without an additional purification.

Benz aldehyde (1.5, 14.10 mmol) was added to acetonitril (50 mL) at 0-10° C., and iodinated ((4,5-dichloro-6-oxopyridazine-1(6H)-yl)methyl)triphenyl phosphonium (8 g, 14.10 mmol) as a crude compound was added to the mixture. The resulting material was stirred for 30 minutes, and potassium t-butoxide (2.05 g, 95%, 17.21 mmol) was added thereto. The mixture was stirred for 2 hours. The solution was concentrated under reduced pressure. Dichloromethane (100 mL) was added, water (50 mL) was added, the solution was stirred for 10 minutes, and neutralized to pH 6.7-7.4 by using a NaHCO$_3$ saturated solution. An organic layer was separated and dried on anhydrous magnesium sulfate. The organic solution was evaporated and concentrated under reduced pressure. The residue was injected into an open-bed silica gel. Column was eluted with methylene chloride/n-hexane (1:4, v/v). Fractions containing trans-isomer were collected, evaporated, and concentrated to obtain pure trans-isomer (Compound 1).

(3) Synthesis of trans-4,5-dichloro-2-styrylpyridazine-3(2H)-one Derivative

Derivatives were prepared according to the same conditions and method as the preparation method of the trans-4,5-dichloro-2-styrylpyridazine-3(2H)-one, except that aldehydes described in Table were used instead of benzaldehyde. Table 1 below shows aldehyde used to prepare respective derivatives.

TABLE 1

| Compound No. | Trans-4,5-dichloro-2-styrylpyridazine-3(2H)-one derivatives | Aldehyde |
| --- | --- | --- |
| 2 | (E)-4,5-dichloro-2-(4-fluorostyryl)pyridazine-3(2H)-one | 4-fluoro benzaldehyde |
| 3 | (E)-4,5-dichloro-2-(4-chlorostyryl)pyridazine-3(2H)-one | 4-chloro benzaldehyde |
| 4 | (E)-2-(4-bromostyryl)-4,5-dichloropyridazine-3(2H)-one | 4-bromo benzaldehyde |
| 5 | (E)-4,5-dichloro-2-(4-Iodostyryl)pyridazine-3(2H)-one | 4-Iodo benzaldehyde |
| 6 | (E)-2-(4-cyanostyryl)-4,5-dichloropyridazine-3(2H)-one | 4-cyano benzaldehyde |
| 7 | (E)-4,5-dichloro-2-(4-methoxycarbonylstyryl)pyridazine-3(2H)-one | 4-methoxycarbonyl benzaldehyde |
| 8 | (E)-4,5-dichloro-2-(2-nitrostyryl)pyridazine-3(2H)-one | 2-nitro benzaldehyde |
| 9 | (E)-4,5-dichloro-2-(3-nitrostyryl)pyridazine-3(2H)-one | 3-nitro benzaldehyde |
| 10 | (E)-4,5-dichloro-2-(4-nitrostyryl)pyridazine-3(2H)-one | 4-nitro benzaldehyde |
| 11 | (E)-4,5-dichloro-2-(4-methylstyryl)pyridazine-3(2H)-one | 4-methyl benzaldehyde |
| 12 | (E)-2-(2-(biphenyl-4-yl)vinyl)-4,5-dichloropyridazine-3(2H)-one | 4-phenyl benzaldehyde |
| 13 | 4,5-dichloro-2-((E)-4-(E)-styrylstyryl)pyridazine-3(2H)-one | 4-styryl benzaldehyde |
| 14 | (E)-4,5-dichloro-2-(4-dimethylamino)styryl)pyridazine- | 4-dimethylamino benzaldehyde |

TABLE 1-continued

| Compound No. | Trans-4,5-dichloro-2-styrylpyridazine-3(2H)-one derivatives | Aldehyde |
|---|---|---|
|  | 3(2H)-one |  |
| 15 | (E)-4,5-dichloro-2-(4-aminostyryl)pyridazine-3(2H)-one | 4-amino benzaldehyde |
| 16 | (E)-4,5-dichloro-2-(2-methoxystyryl)pyridazine-3(2H)-one | 2-methoxy benzaldehyde |
| 17 | (E)-4,5-dichloro-2-(3-methoxystyryl)pyridazine-3(2H)-one | 3-methoxy benzaldehyde |
| 18 | (E)-4,5-dichloro-2-(4-methoxystyryl)pyridazine-3(2H)-one | 4-methoxy benzaldehyde |
| 19 | (E)-4,5-dichloro-2-(2,3-dimethoxy-styryl)pyridazine-3(2H)-one | 2,3-dimethoxy benzaldehyde |
| 20 | (E)-4,5-dichloro-2-(2,4-dimethoxy-styryl)pyridazine- 3(2H)-one | 2,4-dimethoxy benzaldehyde |
| 21 | (E)-4,5-dichloro-2-(2,5-dimethoxy-styryl)pyridazine-3(2H)-one | 2,5-dimethoxy benzaldehyde |
| 22 | (E)-4,5-dichloro-2-(2,6-dimethoxy-styryl)pyridazine-3(2H)-one | 2,6-dimethoxy benzaldehyde |
| 23 | (E)-4,5-dichloro-2-(3,4-dimethoxy-styryl)pyridazine-3(2H)-one | 3,4-dimethoxy benzaldehyde |
| 24 | (E)-4,5-dichloro-2-(3,5-dimethoxy-styryl)pyridazine-3(2H)-one | 3,5-dimethoxy benzaldehyde |
| 25 | (E)-4,5-dichloro-2-(2,3,4-trimethoxystyryl)pyridazine-3(2H)-one | 2,3,4-tiimethoxy benzaldehyde |
| 26 | (E)-4,5-dichloro-2-(2,4,5-trimethoxystyryl)pyridazine-3(2H)-one | 2,4,5-trimethoxy benzaldehyde |
| 27 | (E)-4,5-dichloro-2-(2,4,6-trimethoxystyryl)pyridazine-3(2H)-one | 2,4,6-trimethoxy benzaldehyde |
| 28 | (E)-4,5-dichloro-2-(2,4,5-trimethoxystyryl)pyridazine-3(2H)-one | 3,4,5-trimethoxy benzaldehyde |

Figure 1:
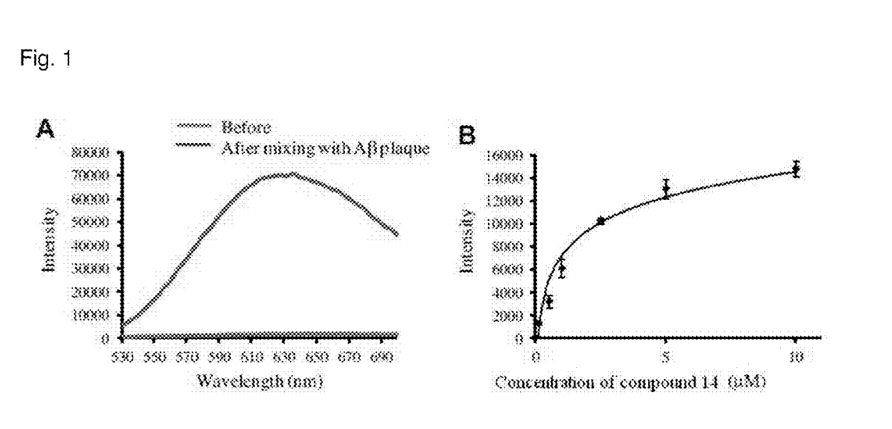
FIG. 1(A) is a graph of fluorescence emission intensity of compound 14 (blue line: before being mixed with Aβ40 aggregates, red line: after being mixed with Aβ40 aggregates)
FIG. 1(B) is a graph of fluorescence intensity according to concentration function of compound 14 under the presence of Aβ40 aggregates.

2. In Vitro Fluorescence Measurement Experiment of 2-styrylpyridazine-3(2H)-one Derivative Fluorescence properties of 28 derivatives (10 μM in PBS) of 2-styrylpyridazine-3(2H)-one were determined by comparing each fluorescence intensity before and after being mixed with agglomerated Aβ40 peptide (10 μM, 35° C., agglomerated in PBS buffer for 3 days.) Nine compounds (Compounds Nos. 14, 15, 17, 18, 19, 20, 25, 27, 28) exhibited an increase in the fluorescence intensity of 10 times or more in the emission spectrum, which means that the compounds were bound with Aβ aggregates (Table 2). Apparent binding constants ($K_d$) of the nine compounds were measured by using 10 μM aggregated Aβ40 peptide. Fluorescence intensity of respective probes of 01, 0.5, 1, 25, 5, and 10 μM dissolved in PBS and fluorescence intensity of a mixture with aggregates Aβ peptide were measured. Compound 14 (FIGS. 1A and 1B) had the highest affinity with respect to Aβ40 ($K_d$=1.84 μM). Theoretically, a preferable fluorescence probe for Aβ aggregates should have high fluorescence reactivity and binding affinity. Fluorescence properties of the fluorescence probe are significantly changed as the probe is bound to the Aβ peptide, and this means that it is 'turned on' according to an interaction with a target. The compound 14 was particularly excellent by detecting Aβ with FAβ/F0=40.84 and $K_d$=1.84 μM.

TABLE 2

| Compound No. | $\lambda_{ex}$ (nm) | $\lambda_{em}$ (nm) | Fold Increase[a] ($F_{A\beta}/F_0$) | $K_d^b$ (mean ± SD) (μM) |
|---|---|---|---|---|
| 1 | 350 | 496 | 4.72 |  |
| 2 | 350 | 492 | 5.93 |  |
| 3 | 380 | 495 | 3.03 |  |
| 4 | 370 | 495 | 2.12 |  |
| 5 | 380 | 498 | 5.26 |  |
| 6 | 380 | 486 | 2.94 |  |
| 7 | 370 | 488 | 2.07 |  |
| 8 | 370 | 500 | 4.12 |  |
| 9 | 390 | 485 | 2.12 |  |
| 10 | 390 | 515 | 2.24 |  |
| 11 | 350 | 516 | 2.81 |  |
| 12 | 380 | 514 | 1.92 |  |
| 13 | 380 | 510 | 2.04 |  |
| 14 | 430 | 636 | 40.84 | 1.84 ± 0.31 |
| 15 | 400 | 598 | 12.15 | 2.95 ± 1.15 |
| 16 | 380 | 492 | 8.24 |  |
| 17 | 350 | 492 | 11.13 | 3.48 ± 1.14 |
| 18 | 400 | 532 | 19.81 | 2.57 ± 0.54 |
| 19 | 350 | 504 | 15.35 | 8.52 ± 2.48 |
| 20 | 400 | 554 | 11.52 | 5.03 ± 3.48 |
| 21 | 370 | 512 | 3.42 |  |
| 22 | 350 | 545 | 4.53 |  |
| 23 | 350 | 552 | 3.52 |  |
| 24 | 350 | 492 | 5.37 |  |
| 25 | 390 | 536 | 26.81 | 4.24 ± 0.98 |
| 26 | 350 | 542 | 3.95 |  |
| 27 | 430 | 560 | 11.72 | 17.55 ± 2.49 |
| 28 | 390 | 580 | 26.12 | 4.14 ± 1.94 |

[a]Fold change values were calculated using fluorescence emission intensity at $\lambda_{em}$ of compounds (using 10 μM compound and 10 μM Aβ40 aggregates).
[b]$K_d$ value was indicated as mean ± SD, which is obtained from three independent replicates (N = 3.)

3. Imaging Fluorescence of Intracellular Aβ Aggregates

Figure 2:
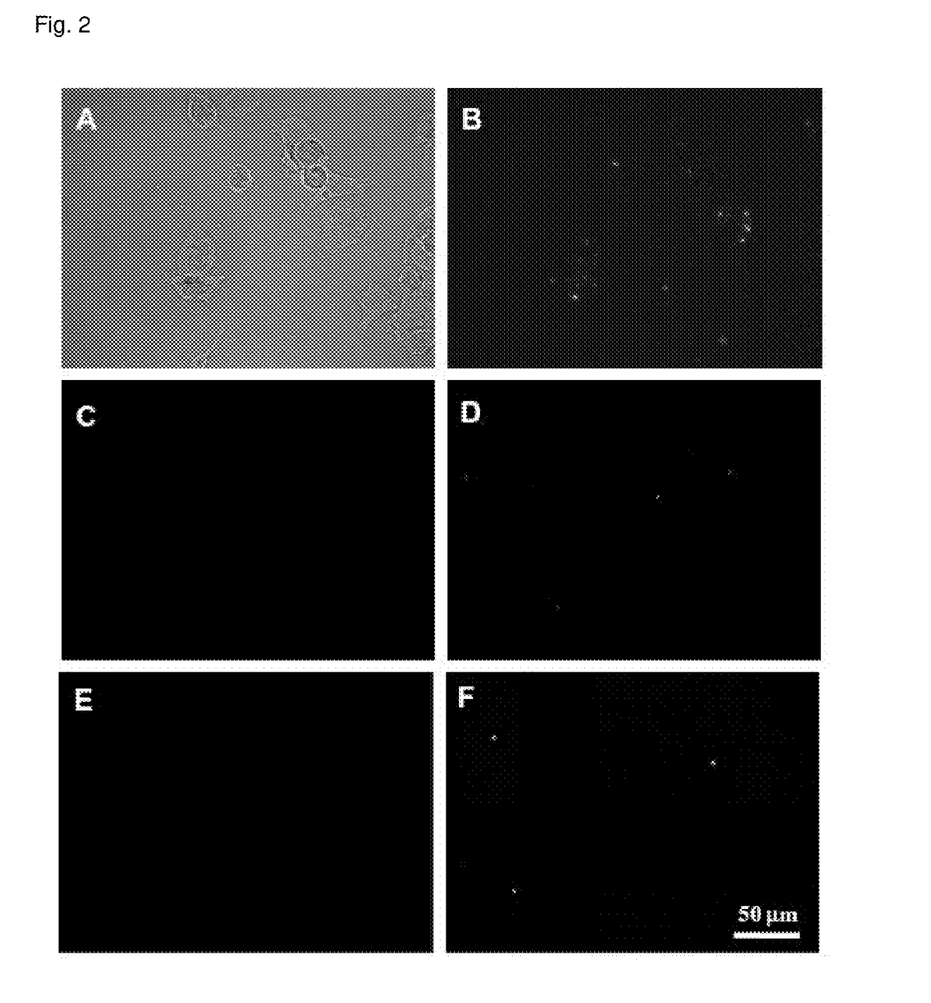
FIG. 2 shows cellular uptake of FITC-Aβ42:
(A) SHSY5Y cell
(B) Microscope fluorescence image of SHSY5Y cell cultured with 1 μM of FITC-Aβ42 for three days
(C) Microscope fluorescence image of SHSY5Y cell extract (culture without Aβ42+ staining with compound 14)
(D) Microscope fluorescence image of SHSY5Y cell extract (culture with Aβ42+ staining with compound 14)
(E) Microscope fluorescence image of SHSY5Y cell extract (culture without Aβ42+ staining with thio-flavine T)

Fluorescence imaging of compound 14 was performed on intracellular Aβ aggregates of a SHSY5Y neuroblastoma cell. In order to measure intracellular uptake and aggregation of Aβ, 1 μM of Aβ42 (FITC-Aβ42) labelled with fluorescein isothiocyanate was added, and SHSY5Y cell was cultivated 3 days and imaged with fluorescence microscope. Uptake of FITC-Aβ42 in the SHSY5Y cell was observed (FIG. 2B). The conventional research reported that, after extracellular soluble Aβ is taken up, Aβ42 aggregates (>200 kDa) having a high molecular weight is formed. In order to determine whether the compound 14 is used as a fluorescence probe component for detecting intracellular Aβ aggregates, a cell having unlabelled Aβ42 added thereto was sonicated with SDS, and the homogenate was reacted with 10 μM of compound 14 for 10 minutes. Fluorescence precipitate was obtained from the Aβ added cell extract (FIG. 2D). The labelled pattern was identical to a pattern observed by using thio-flavine T (FIG. 2F). An extract of a cell grown without Aβ did not have fluorescent staining (FIGS. 2C and 2E). This result strongly implies that 2-styrylpyridazie-3(2H)-one-based probe can stain intracellular Aβ aggregates.

4. Fluorescence Imaging of In Vivo Brain Tissue

Figure 3:
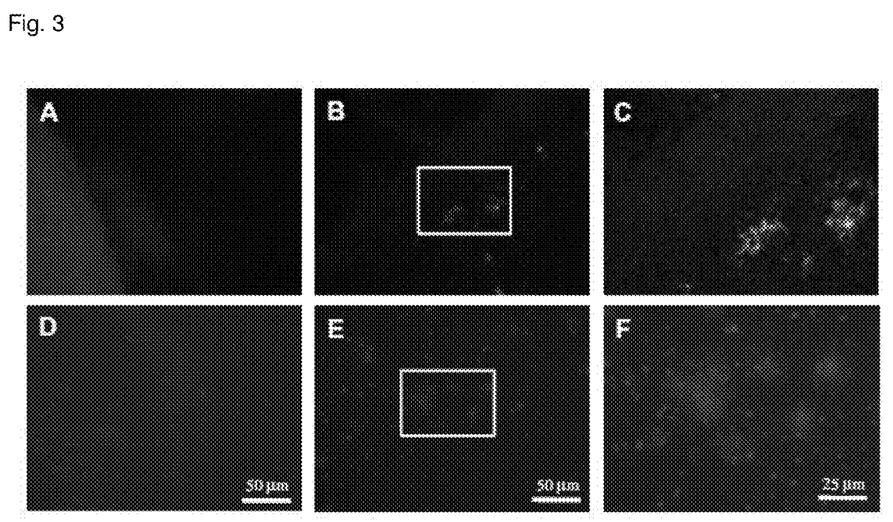
FIG. 3 shows stained tissues of a brain section of a mouse (A) A control group mouse, staining with compound 14
(B) APP/SP1 transgenic AD model mouse, staining with compound 14
(C) APP/SP1 transgenic AD model mouse, staining with compound 14
(D) A control group mouse, staining with thio-flavine T
(E) APP/SP1 transgenic AD model mouse, staining with thio-flavine T
(F) APP/SP1 transgenic AD model mouse, staining with thio-flavine T

In order to evaluate whether 2-styrylpyridazine-3(2H)-one-based compound 14 can stain beta amyloid aggregates of brain tissues of an AD mouse, compound 14 was tested in a brain section of an 15-month aged transgenic AD mouse (APP/PS 1) model. FIG. 3 shows a representative fluorescence microscope photograph of these tissue samples. Aβ aggregates were clearly stained by compound 14, and this result corresponds to the high affinity of compound 14 to the Aβ aggregates appearing in the in vitro experiment (FIGS. 3B and 3C). Labelled pattern corresponded to a signal obtained from a standard section (FIGS. 3E and 3F) stained with thio-flavine T. Meanwhile, tissues of a general house were not stained with the compound 14 or thio-flavine T (FIGS. 3A and 3D). This result implies that compound 14 can serve as a probe for detecting Aβ aggregates in a brain.

Conventionally, a stilbene derivative was known as a legand having high binding affinity with respect to Aβ aggregates. Recently, two structurally similar compounds have been developed as commercial probes BAY 94-9172 and AV-45, and these two types of molecules have a rigid structure of stilbene (BAY 94-9172) and styrylpyridin (AV-45). The inventors of the present application prepared styrylpyridazine-3(2H)-one by substituting a phenyl group of stilbene to develop a fluorescence marker for detecting Aβ aggregates. Also, all the PET imaging probes (BAY 94-9172, AV-45, and GE067) in a clinical test contain monomethylamino group or dimethylamino group providing binding specificity with respect to Aβ aggregates.

In conclusion, the inventors of the present application revealed that 2-styrylpyridazine-3(2H)-one derivative (compound 14) containing dimethylamino group has fluorescence properties most appropriate for imaging Aβ aggregates. In particular, compound 14 exhibited very strong fluorescence reactivity ($F_{A\beta}/F_0$=40.84) and binding affinity ($K_d$=1.84 μM) with respect to Aβ aggregates, and clearly stained intracellular Aβ aggregates and Aβ aggregates of the transgenic AD mouse model (APP/PS1). Therefore, obviously, the 2-styrylpyridazine-3(2H)-one derivatives containing compound 14 are an excellent candidate material as a fluorescence imaging agent for AD research.

The foregoing embodiments and advantages are merely exemplary and are not to be considered as limiting the present invention. The present teachings can be readily applied to other types of apparatuses. This description is intended to be illustrative, and not to limit the scope of the claims. Many alternatives, modifications, and variations will be apparent to those skilled in the art. The features, structures, methods, and other properties of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds are therefore intended to be embraced by the appended claims.

The invention claimed is:

1. A method for detecting beta amyloid aggregates in a subject comprising,
    (i) administering to said subject a 2-styrylpyridazine-3(2H)-one derivative of formula (1) or its pharmaceutically acceptable salt wherein n is an integer of 1 to 3,
    each R is independently selected from the group consisting of halogen, cyano, substituted or unsubstituted carbonyl, nitro, substituted or unsubstituted $C_1$-$C_{10}$ alkyl, substituted or unsubstituted phenyl, substituted or unsubstituted $C_1$-$C_{10}$ alkenyl, substituted or unsubstituted amino, and substituted or unsubstituted $C_1$-$C_{10}$ alkoxy;
    (ii) permitting sufficient time for said derivative or salt to bind any amyloid aggregates; and
    (iii) imaging fluorescence of the bound derivative or salt; thereby detecting amyloid aggregates in said subject.

2. The method of claim 1, wherein each R is independently selected from the group consisting of halogen, cyano, $C_1$-$C_3$ alkoxy carbonyl, nitro, $C_1$-$C_3$ alkyl, phenyl, phenylvinyl, $C_1$-$C_3$ dialkyl amino, amino, and $C_1$-$C_3$ alkoxy.

3. The method of claim 1, wherein the 2-styrylpyridazine-3(2H)-one derivative is (E)-4,5-dichloro-2-(4-(dimethylamino)styryl)pyridazine-3(2H)-one.

4. A method for diagnosing beta amyloid aggregation disease in a subject comprising,
    (i) administering to said subject a 2-styrylpyridazine-3(2H)-one derivative of formula (1) or its pharmaceutically acceptable salt;

wherein n is an integer of 1 to 3,
    each R is independently selected from the group consisting of halogen, cyano, substituted or unsubstituted carbonyl, nitro, substituted or unsubstituted $C_1$-$C_{10}$ alkyl, substituted or unsubstituted phenyl, substituted or unsubstituted $C_1$-$C_{10}$ alkenyl, substituted or unsubstituted amino, and substituted or unsubstituted $C_1$-$C_{10}$ alkoxy;
    (ii) permitting sufficient time for said derivative or salt to bind any amyloid aggregates; and
    (iii) imaging fluorescence of the bound derivative or salt; thereby detecting amyloid aggregates in said subject thus diagnosing amyloid aggregation disease in said subject.

5. The method of claim 4, wherein each R is independently selected from the group consisting of halogen, cyano, $C_1$-$C_3$ alkoxy carbonyl, nitro, $C_1$-$C_3$ alkyl, phenyl, phenylvinyl, $C_1$-$C_3$ dialkyl amino, amino, and $C_1$-$C_3$ alkoxy.

6. The method of claim 4, wherein the 2-styrylpyridazine-3(2H)-one derivative is (E)-4,5-dichloro-2-(4-(dimethylamino)styryl)pyridazine-3(2H)-one.

7. The method of claim 4, wherein the beta amyloid aggregation disease is selected from the group consisting of dementia, Alzheimer's disease, Down's syndrome, amyloid angiopathy, cerebral amyloid angiopathy, generalized amyloidosis, Dutch type amyloidosis, inclusion-body myositis, Mediterranean fever, Muckle-Wells syndrome, idiopathic myeloma, amyloid polyneuropathy, amyloid cardiomyopathy, generalized senile amyloidosis, amyloidosis hereditary cerebral hemorrhage, Down's syndrome, scrapie, Creutzfeldt-Jakob disease, kuru disease, Gerstmann Sträussler Scheinker syndrome, medullary carcinoma, muscular atrophy disease, and Langerhans islets II-type diabetes mellitus.

* * * * *